United States Patent [19]

Kasai et al.

[11] Patent Number: 5,201,794
[45] Date of Patent: Apr. 13, 1993

[54] METHOD FOR SAMPLING BLOOD SPECIMEN

[75] Inventors: Masaaki Kasai; Sakae Yamazaki, both of Nakakoma, Japan

[73] Assignee: Terumo Kabushiki Kaisha, Tokyo, Japan

[21] Appl. No.: 830,992

[22] Filed: Feb. 5, 1992

Related U.S. Application Data

[63] Continuation of Ser. No. 449,892, filed as PCT/JP88/00605, Jun. 17, 1988, abandoned.

[30] Foreign Application Priority Data

Jun. 18, 1987 [JP] Japan .................. 62-150241

[51] Int. Cl.⁵ .............................................. G01N 1/00
[52] U.S. Cl. ................................................ 73/863.01
[58] Field of Search ... 73/863.01, 864, 864.21-864.24, 73/864.83, 864.86, 864.52; 220/DIG. 19, 352, 353, 354; 215/355-363, 247-249, DIG. 3; 604/415, 201

[56] References Cited

U.S. PATENT DOCUMENTS

| | | | |
|---|---|---|---|
| 2,457,120 | 12/1948 | Brandon | 215/247 |
| 2,734,649 | 2/1956 | Callahan et al. | 215/DIG. 3 |
| 3,092,278 | 6/1963 | Jarnhall | 215/DIG. 3 |
| 3,198,368 | 8/1965 | Kirkland et al. | 215/DIG. 3 |
| 3,424,329 | 1/1969 | Hershberg et al. | 215/DIG. 3 |
| 3,463,339 | 8/1969 | McGuckin | 215/247 |
| 3,748,911 | 7/1973 | Rousselet et al. . | |
| 3,872,730 | 3/1975 | Ringrose et al. | 73/864.23 |
| 4,248,355 | 2/1981 | Kolb et al. . | |
| 4,254,884 | 3/1981 | Maruyama | 215/247 |
| 4,301,936 | 11/1981 | Percarpio | 215/247 |
| 4,338,764 | 7/1982 | Percarpio . | |
| 4,342,341 | 8/1982 | Lee . | |
| 4,478,095 | 10/1984 | Bradley et al. | 73/864.23 |
| 4,577,514 | 3/1986 | Bradley et al. | 73/863.01 |
| 4,652,429 | 3/1987 | Konrad | 215/249 |
| 4,682,703 | 7/1987 | Kasai . | |
| 4,811,611 | 3/1989 | Uffenheimer | 73/864.22 |
| 4,873,875 | 10/1989 | Cork | 73/863.01 |

FOREIGN PATENT DOCUMENTS

| | | | |
|---|---|---|---|
| 0059297 | 9/1982 | European Pat. Off. . | |
| 0199356 | 10/1986 | European Pat. Off. . | |
| 2834186 | 8/1979 | Fed. Rep. of Germany . | |
| 48-20157 | 6/1973 | Japan . | |
| 0039185 | 4/1978 | Japan | 73/863.01 |
| 57-113364 | 7/1982 | Japan . | |
| 59-638 | 1/1984 | Japan . | |
| 59-55240 | 3/1984 | Japan . | |
| 59-187262 | 10/1984 | Japan . | |
| 60-13465 | 1/1985 | Japan . | |
| 60-27836 | 2/1985 | Japan . | |
| 0108754 | 6/1985 | Japan | 73/863.01 |
| 61-2037 | 1/1986 | Japan . | |
| 2071066 | 9/1981 | United Kingdom | 215/247 |

Primary Examiner—Robert Raevis
Attorney, Agent, or Firm—Frishauf, Holtz, Goodman & Woodward

[57] ABSTRACT

In sampling a blood specimen inside a blood-collecting tube equipped with a film stopper at an opening thereof, a needle capable of sampling a blood component is made to pierce the film stopper and the tip of the needle is situated in the blood specimen. The blood specimen is sampled via the needle while the interior of the blood-collecting tube is kept cut off from the exterior thereof.

5 Claims, 6 Drawing Sheets

METHOD FOR SAMPLING BLOOD SPECIMEN

This application is a continuation of application Ser. No. 07/449,842, filed as PCT/JP88/00605, Jun. 17, 1988, abandoned.

TECHNICAL FIELD

This invention relates to a method and apparatus for sampling a blood speciment in blood testing.

BACKGROUND ART

The following procedure ordinarily is adopted when attempting to sample a serum specimen in a blood test:

First, blood is collected from a vein using a blood-collecting tube 80 (sealed by a rubber stopper 81), of the kind shown in FIG. 7, the interior of which is depressurized with respect to the atmosphere. Thereafter, the blood is subjected to centrifugal separation when it coagulates sufficiently.

In order to extract a specimen solely from the serum layer obtained by separation, decantation or a sampling method using a pipette are available.

Decantation refers to a method in which the rubber stopper is removed and only the serum from the upper layer is poured into a separate tube by hand. This state is illustrated in FIG. 8(a).

In the method using a pipette, a pipette is inserted into the blood-collecting tube 80 via the opening from which the rubber stopper has been removed, and only the serum is sampled by the pipette. This state is shown in FIG. 8(b). Apparatus for performing these operations automatically are also available.

In any case, it is necessary to remove the rubber stopper when sampling serum. When attempting to sample serum, therefore, some of the blood naturally spills out, and there is the danger that impurities will pierce the interior of the blood-collecting tube from the outside. Thus, major problems remain.

In particular, when separated serum is divided several times for testing, sampling must be performed by repeating these sampling methods several times. This increases the possibility that the aforementioned difficulties will be encountered.

SUMMARY OF THE INVENTION

The present invention has been devised in view of this prior art and attempts to provide a blood specimen sampling method and apparatus in which a process from blood collecting until sampling of an objective blood specimen is performed while a blood-collecting tube is kept closed, whereby the specimen inside the tube will not be spilled carelessly and impurities from the outside will not mix in with the specimen during this process.

In order to solve the foregoing problems, the blood specimen sampling method of the present invention comprises the steps set forth below.

Specifically, there is provided a blood specimen sampling method used in order to sample a blood specimen from a blood-collecting tube equipped with a film stopper, which comprises a gas-barrier film layer and a layer, at an opening thereof, comprising:

a step of introducing a needle into the interior of the blood-collecting tube by piercing the film stopper thereof, a step of drawing in a blood specimen from a distal end of the needle, which has pierced the film stopper owing to the foregoing step, after the distal end is at least situated in the blood specimen.

In accordance with a preferred embodiment of the invention, it is desirable that the method include a step of piercing the film stopper with an air-introducing needle at least before the blood specimen is drawn in. This introduces air into the blood-collecting tube from the outside to facilitate the sampling of the blood specimen.

The blood specimen sampling apparatus of the present invention has the construction set forth below.

Specifically, there is provided a blood specimen sampling apparatus used in order to sample a blood specimen from a blood-collecting tube equipped with a film stopper, which comprises a gas-barrier film layer and a resealable layer, at an opening thereof, comprising:

holding means for holding the blood-sampling tube, in which blood has been collected, in a substantially upright state;

sampling means having a needle capable of sampling the blood inside the held blood-collecting tube upon piercing the film stopper thereof;

detecting means for detecting that a distal end of the needle, which has been caused to pierce the film stopper by the sampling means, is at least situated in the blood specimen; and suction means for drawing in the blood specimen from the distal end of the needle in accordance with information detected by the detecting means.

In accordance with a preferred embodiment of the invention, it is desirable that the sampling means include an air-introducing needle capable of introducing air into the blood-collecting tube from the outside thereof. This will make it possible to introduce air into the blood-collecting tube from the outside to facilitate the sampling of the blood specimen.

In accordance with a preferred embodiment of the invention, the blood specimen sampled is serum, and the detecting means detects an interface between a blood serum layer and a clot layer. The piercing operation of the sampling means is halted based on the results of detection performed by the detecting means. This facilitates situating the sampling means at the position of the serum layer.

In accordance with a preferred embodiment of the invention, detection of the interface between the blood serum layer and the clot layer is performed by blood serum separating means such as a blood separating agent or blood separating float, and the detecting means detects the blood serum separating means. This makes it possible to detect the interface between the blood serum layer and the clot layer.

DETAILED DESCRIPTION

An embodiment of the present invention will now be described in detail in accordance with the accompanying drawings.

Figure 1:
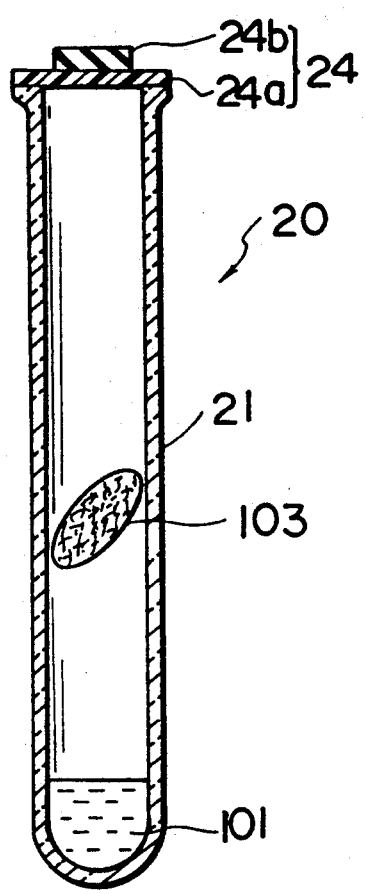
FIG. 1 is a view illustrating the structure of a blood-collecting tube in an embodiment.
Figure 2:
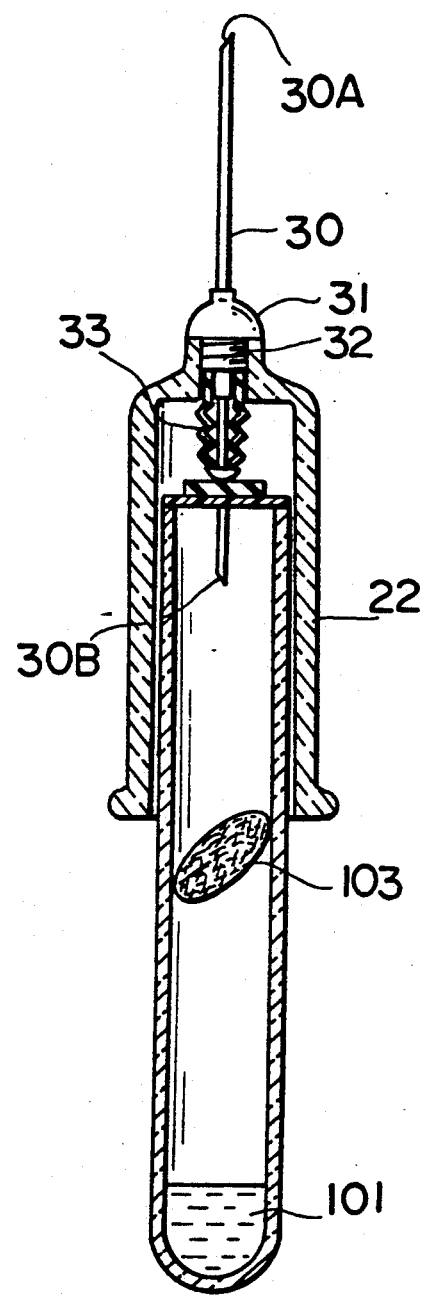
FIG. 2 is a view showing a blood-sampling tube inserted in a blood sampling holder.
Figure 3:
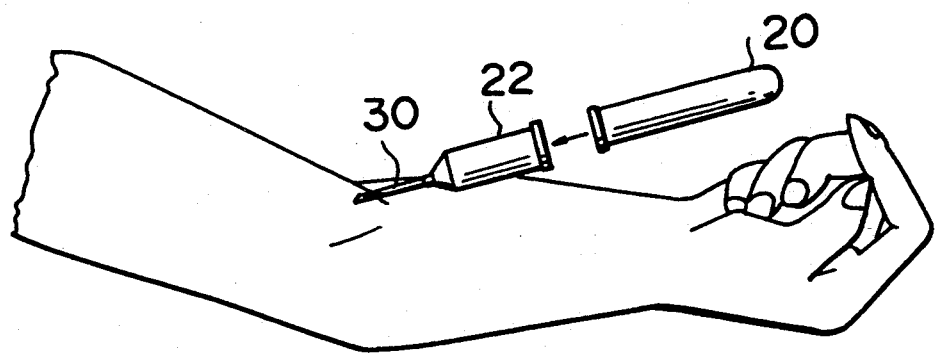
FIG. 3 is a view showing blood being collected by the blood-collecting tube of the embodiment.

Description of Blood-Collecting Processing (FIGS. 1–3)

FIG. 1 is a sectional view of a blood-collecting tube.

In this embodiment, the blood-collecting tube 20 is composed of a tube body 21 and a film stopper 24. The tube 20 is evacuated to negative pressure before blood is sampled from a living body. The structure of the stopper 24 will be described later.

FIG. 2 is a view showing the blood-collecting tube of the embodiment when in use, and FIG. 3 is a view showing a state in which blood is sampled in accordance with the embodiment.

The constituents and actions of the embodiment will now be described in due course.

Numeral 22 denotes a blood-collecting holder having an opening into which the blood-collecting tube 20 is inserted. The blood-collecting holder 22 has a piercing needle 30 (hollow) which is secured by screwing a hub 31 onto a threaded portion 32 formed on the holder 22. A tip 30A of the piercing needle 30 having a pointed end to facilitate piercing of a living body. The piercing needle 30 has another end 30B also equipped with a pointed tip capable of piercing the film stopper 24 of the blood-collecting tube 20. The pointed end 30B is covered by a sheath-shaped flexible rubber cap 33.

When blood is actually collected in the blood-collecting tube, first the blood-collecting holder 22 is used to pierce the living body (a vein), after which the film stopper 24 of the blood-collecting tube 20 is inserted into the holder from the opening thereof so that the pointed end 30B of the piercing needle pierces into the blood-collecting tube 20, whereby blood is collected.

The structure of the blood-collecting tube of the embodiment will now be described.

As for the film stopper provided in the opening of the blood-collecting tube used particularly in this embodiment, use is made of one which, unlike the conventional rubber stopper, is capable of being pierced by the needle body of the blood specimen sampling apparatus and is thin enough so that the needle will not bend when piercing the stopper.

Preferably, the film stopper comprises a laminated body of a gas-barrier film having a thickness of 20–200 μm and vulcanized rubber having a thickness of 0.3–2 mm.

The tube body 21 of the blood-collecting tube in this embodiment is made of an acrylonitrile resin and is formed by an extrusion blowing method (overall length: 100 mm, outer diameter: 14.4 mm, inner diameter: 13.4 mm). The film stopper 24 includes a gas barrier film 24a, made of an acrylonitrile resin (brand name: Varex 210, manufactured by Mitsui Toatsu) 30 μm/vapor deposited aluminum/nylon 15 μm) that is heated and caused to fuse with the opening of the tube body 21 under reduced pressure, and a natural rubber sheet 24b (diameter: 8 mm), having a thickness of approximately 1 mm, bonded to the film by rubber cement. There is no limitation upon the material used to fabricate the tube body 21, and it will suffice if the material has a gas-barrier property. Accordingly, the material can be polyethylene, glass, etc.

In accordance with this arrangement, a liquid-tight state can be maintained between the interior and exterior of the blood-collecting tube even if the piercing needle is removed after it has pierced the film stopper 24.

A serum-separating agent 101 whitened by titanium white the main ingredient of which is α-olefin-dialkyl-maleate copolymer is placed inside the tube body of the blood-collecting tube in this embodiment. Further, an unwoven fabric 103 coated with a coagulating-promoting agent is inserted in the tube body.

Figure 4:
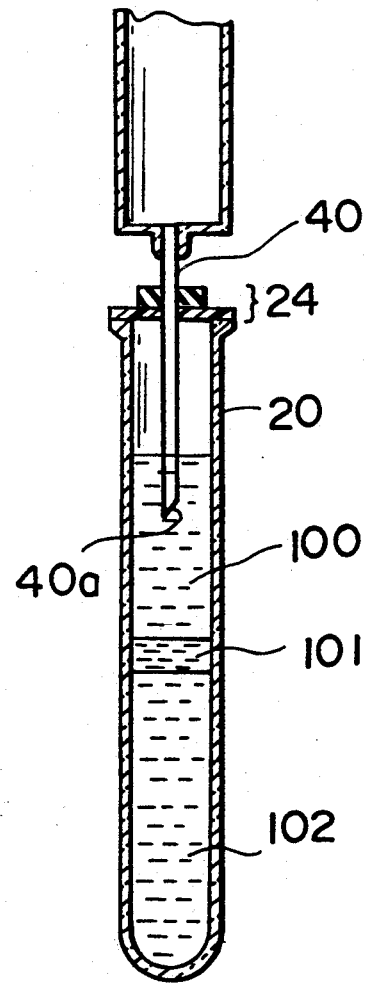
FIG. 4 is a view showing a serum sampling method.

Description of Serum Sampling Processing (FIG. 4)

After blood has been sampled and collected in the blood-collecting tube 20 described above, centrifugal separation is applied following coagulation of the blood. A serum layer 100 is produced by this processing. In sampling the serum in this embodiment, the sampling is performed with the blood-collecting tube 20 kept sealed, without using decantation or a pipette. Specifically, after, say, an 18 G syringe needle 40 pierces the film stopper 24 from the upper portion of the blood-collecting tube 20 and the needle tip (a cutting edge) reaches the serum layer, a predetermined amount of the serum is sampled (FIG. 4).

Here the piercing resistance between the film stopper 24 and the syringe needle 40 can be a problem. In the present embodiment, however, the piercing resistance between the film stopper 24 and the syringe needle 40 is about 550 g and no difficulties are encountered. By way of example, the piercing resistance in a case where use is made of a stopper consisting of vulcanized butyl rubber or the like is as high as about 2100 g. With such a stopper, problems would arise such as bending of the syringe needle.

The relationship between piercing resistance and the composition of the stopper used in serum sampling in this embodiment is shown in the table below, which illustrates average values each obtained from measuring piercing resistance five times. Further, A, B and C are shown in the evaluation column, in which A means that the syringe needle did not bend even after performing sampling using 100 blood-collecting tubes, B means that sampling is possible 50 times, and C means that sampling cannot be performed even 10 times.

| COMPOSITION OF SEAL | AVERAGE PIERCING RESISTANCE (N = 5) | EVALUATION |
| --- | --- | --- |
| VAREX 30 μm/VAPOR-DEPOSITED ALUMINUM/NYLON 15 μm/NATURAL RUBBER 1 mm | 550 g | A |
| VULCANIZED BUTYL RUBBER STOPPER | 2100 g | C |
| VAREX 80 μm/ALUMINUM FOIL 50 μm/NYLON 20 μm/NATURAL RUBBER 1 mm | 700 g | A |
| VAREX 80 μm/ALUMINUM FOIL 50 μm/NYLON 20 μm/NATURAL RUBBER 3 mm | 1400 g | B |
| VAREX 150 μm/ALUMINUM FOIL 50 μm/NYLON 30 μm/NATURAL RUBBER | 1300 g | B |

| COMPOSITION OF SEAL | AVERAGE PIERCING RESISTANCE (N = 5) | EVALUATION |
|---|---|---|
| 3 mm | | |

A: 100 blood-collecting tubes can be pierced with one needle
B: 50 blood-collecting tubes can be pierced with one needle, but piercing 100 is impossible
C: 10 blood-collecting tubes cannot be pierced with one needle The table demonstrates that there is no limitation upon the composition of the stopper 24 described above. Specifically, it is permissable to bond aluminum foil (50 μm) instead of depositing aluminum. Preferably, the film stopper comprises a gas-barrier film having a thickness of 10-200 μm and vulcanized rubber or elastomer having a thickness of 0.3-2 mm. A gas-barrier film whose thickness is less than 10 μm is too weak in strength, while one whose thickness is greater than 200 μm offers too much piercing resistance and has adverse effects both at the time of collecting blood and at the time of sampling.

If the thickness of the vulcanized rubber or elastomer, which is for providing resealability, is less than 0.3 mm, the result will be a poor resealing property; a thickness in excess of 2 mm results in too much piercing resistance.

It is permissible for the sampling needle to have a sharp, closed tip, with a hole being provided in the side thereof.

As for the location pierced by the sampling needle, any point having the resealing rubber will suffice, though it is permissible to pierce the film portion. By piercing the film portion, a hole will be formed at the piercing since the film portion does not possess resealability. As a result, there will be no seal between the sampling needle and the hole and air from the outside will flow into the blood-collecting tube via the gap. Consequently, negative pressure will not develop inside blood-collecting tube at the time of sampling. In other words, the sampling operation can not be performed smoothly.

Figure 5:
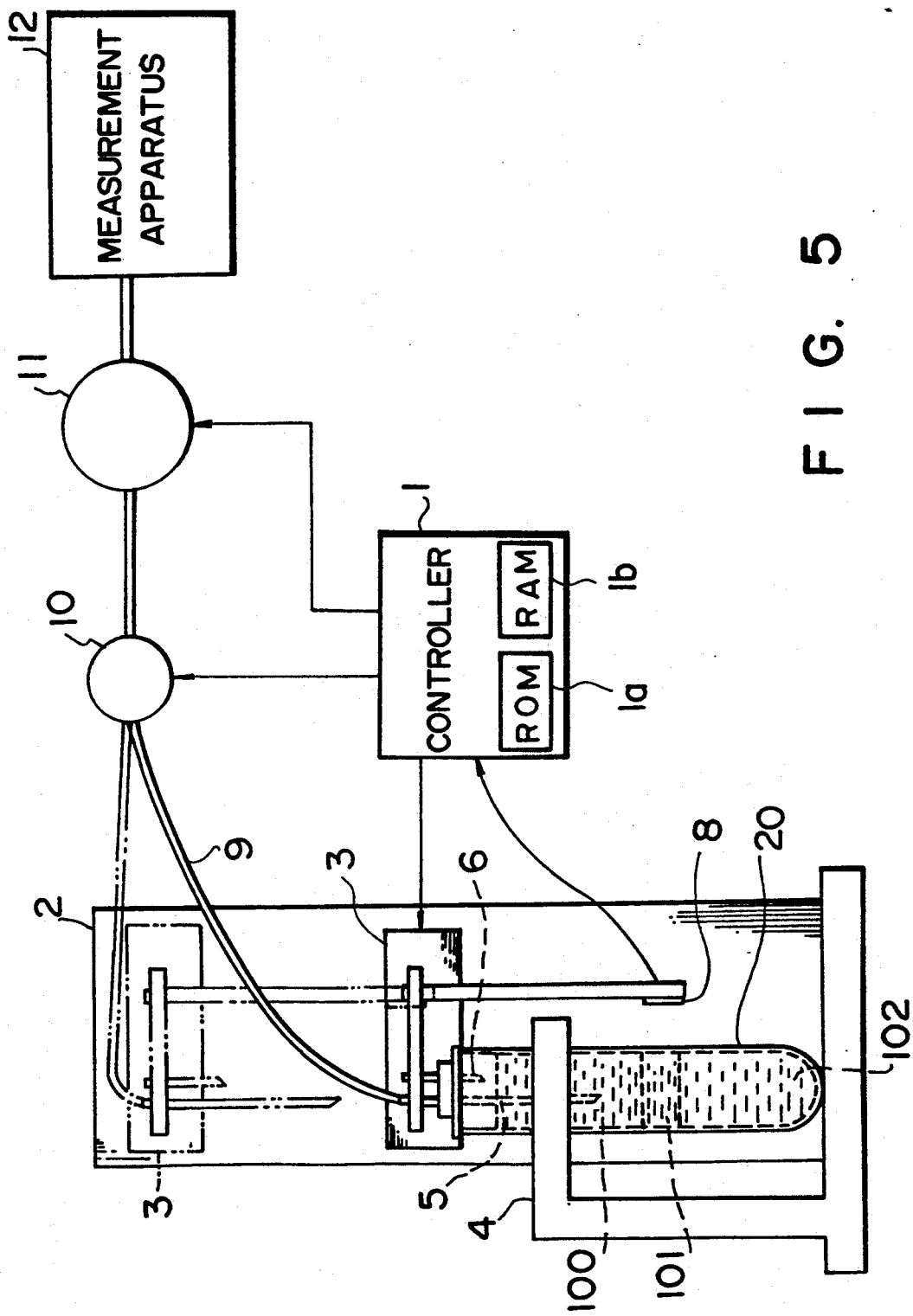
FIG. 5 is a view showing the essentials of a serum sampling apparatus.
Figure 6:
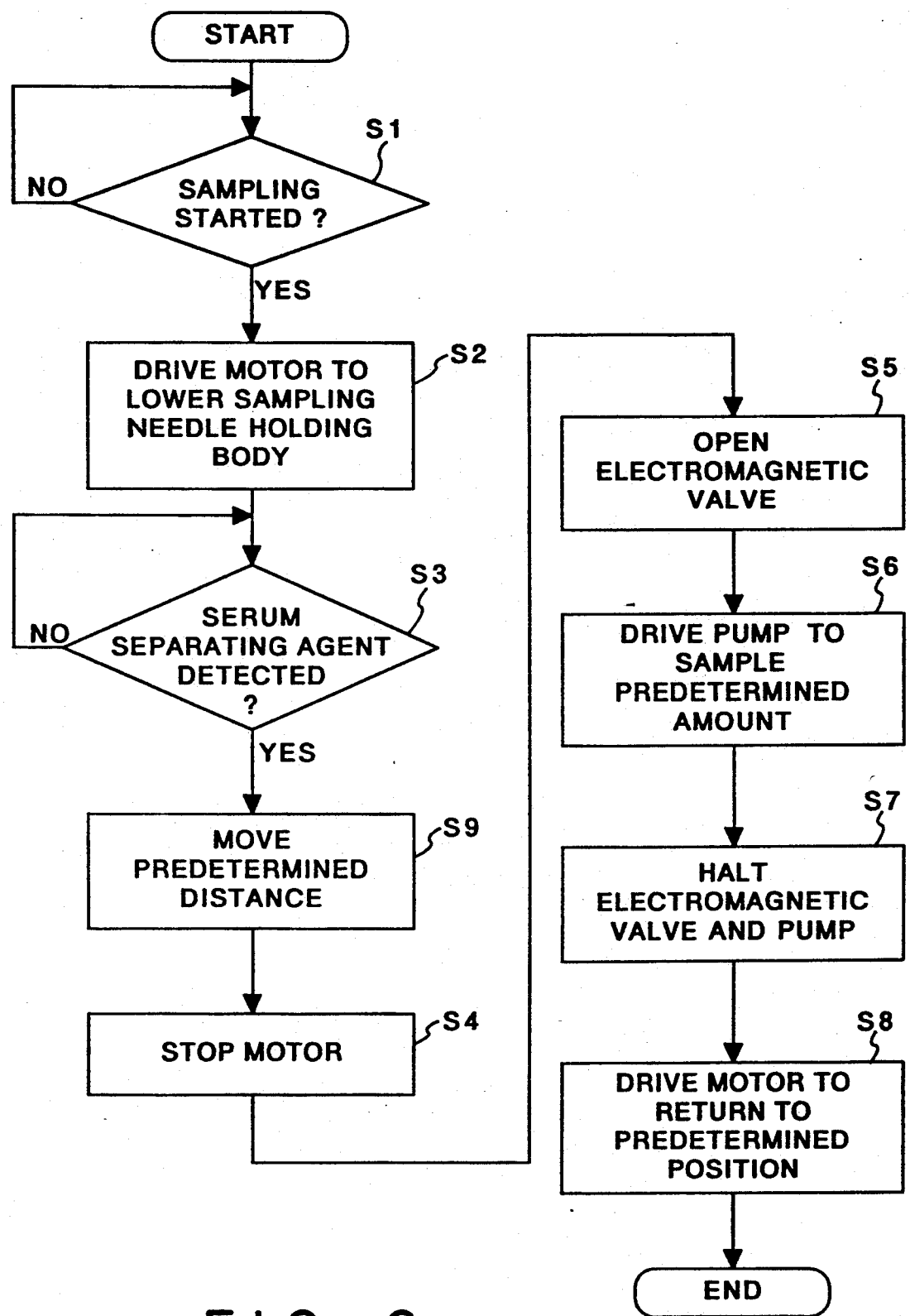
FIG. 6 is a flowchart for describing the operation of a controller in FIG. 5.

Description of Serum Sampling Apparatus (FIGS. 5, 6)

The apparatus for executing the foregoing sampling processing will now be described.

FIG. 5 illustrates the relationship between the serum sampling apparatus and a measurement section for analytically measuring the serum sample.

Figure 7:
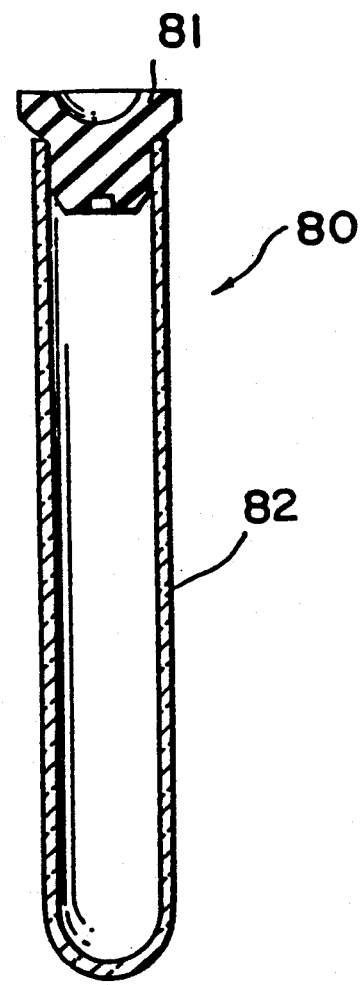
FIG. 7 is a sectional view of a conventional blood-collecting tube.
Figure 8B:
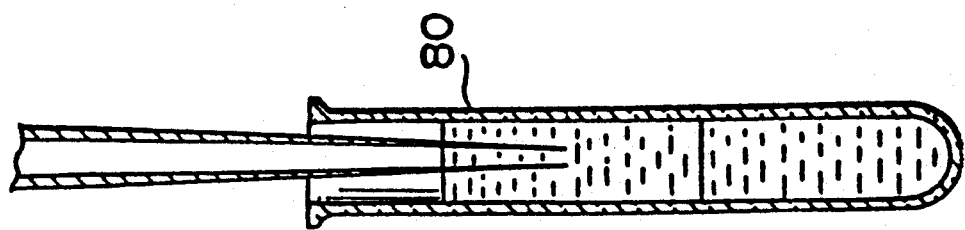
FIG. 8(b) is a view for describing a method of sampling serum using a pipette.
Figure 8A:
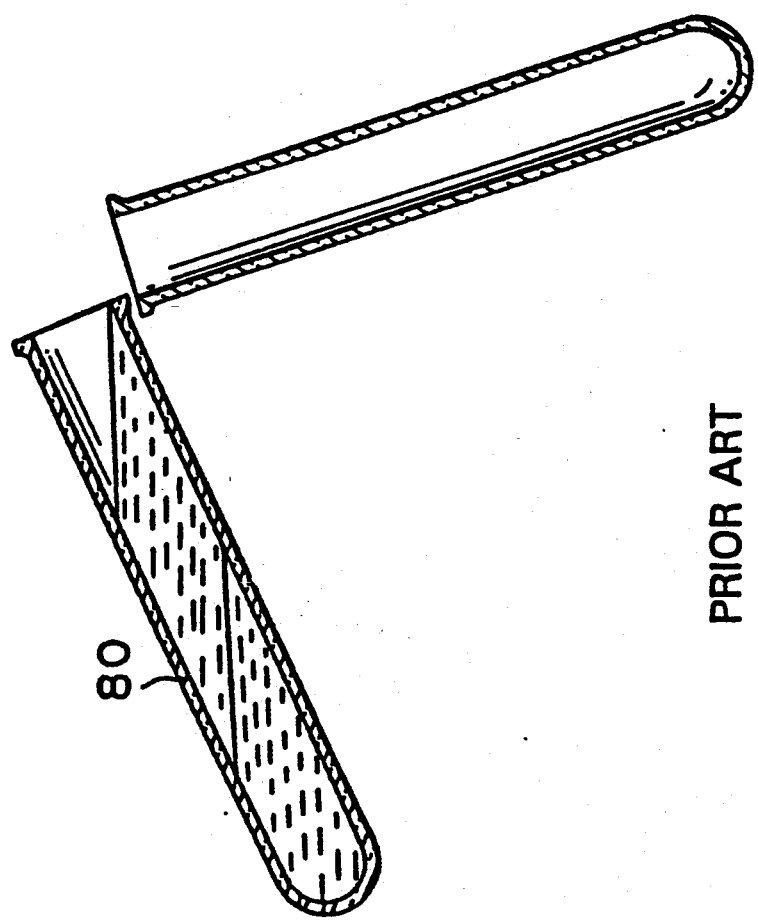
FIG. 8(a) is a view showing a method of sampling serum by a decantation operation.

In FIG. 5, numeral 1 denotes a controller for controlling the overall sampling apparatus and having internally a ROM 1a storing the operating procedure (see the flowchart of FIG. 7) and a RAM 1b used as a working area. Numeral 2 denotes a sampling base having a fixed portion 4 for fixing the blood-collecting tube 20. The sampling base 2 has a holding body 3 for fixedly holding a sampling needle 5 (hollow) having a pointed end for extracting serum from the blood-collecting tube 20, an air needle 6 (the interior of which is hollow) having similarly shaped tip for supplying air from the outside, and a sensor unit 8 equipped with a sensor at its distal end in order to detect a serum separating agent. The holding body 3 is moved up and down by a motor, not shown. Numeral 9 denotes a tube for introducing sampled serum, 10 an electromagnetic valve, 11 a rotary-type pump, and 12 a measurement section for measuring and analyzing sampled serum.

Ordinarily, the amount of blood collected inside the blood-collecting tube 20 is substantially constant. Therefore, when the sensor unit 8 senses the serum-separating agent 101, the positional relationship among the components is fixed in advance in such a manner that the tip of the sampling needle 5 will be situated within the serum layer 100 and the air needle 6 is situated in the air space of the blood-collecting tube 20. Numeral 102 denotes a clot layer.

The operating process of the serum sampling apparatus in the embodiment thus constructed will now be described in accordance with the flowchart of FIG. 6. It is assumed that the holding body 3 is at the position of the broken line in FIG. 5 before the measurement operation starts.

First, when the blood-collecting tube 20 in which the serum layer 100 has been produced by centrifugal separation is secured to the fixed portion 4, the holding body 3 is at rest (step S1) at the position of the broken line in the drawing until a start switch, not shown, is operated. Rather than relying upon a start switch, it is permissible to provide a sensor which senses that the blood-collecting tube 20 has been secured to (or placed on) the fixed portion 4, with sampling being started in response to a signal from this sensor.

In any case, when the start of operation has been instructed, the program proceeds to step S2, at which a motor (not shown) is driven to move the holding body 3 downward. During downward movement of the holding body 3, the controller 1 is receiving a signal from the sensor of the sensor unit 8, with downward movement continuing until the serum-separating agent 101 (white in color) is detected (step S3). When a signal is received from the sensor unit 8 indicating that the serum-separating agent has been detected, the holding body is moved by an amount equal to the difference in distance between the sensor unit and the tip of the needle (step S9). The motor is stopped at step S4 to halt movement of the holding body 3. Thereafter, the electromagnetic valve 100 is opened (step S5) and processing for driving the pump is executed (step S6) to supply a predetermined amount of serum to the measurement section 12. This is followed by stopping the pump 11 and the electromagnetic valve 10 (step S7). Now the motor is driven to return the holding body 3 to its starting position, with the motor being stopped when the starting position is attained (step S8). Preparations are then made for the next specimen via a cleansing mechanism. The serum can be divided up without it reaching the measuring device.

In accordance with the blood specimen sampling method of the invention as described above, the blood-collecting tube is kept in a closed state from the time blood is collected until the objective blood specimen is sampled from the blood-collecting tube. During this time, therefore, the blood specimen inside the blood-collecting tube will not spill out and foreign matter will not mix in from the outside.

Further, in accordance with the blood specimen sampling apparatus of the invention, besides obtaining the foregoing advantages it is also possible to extract the blood component automatically, thereby raising operating efficiency by a wide margin.

Furthermore, sampling of serum is facilitated by introducing an air needle into the blood-collecting tube.

We claim:
1. A blood specimen sampling method for sampling a blood specimen from a blood-collecting tube having a film stopper at an opening portion thereof, said method comprising:

providing a blood-collecting tube having a film stopper fused to an opening portion thereof, said film stopper comprising a gas-barrier film layer having a thickness of 10–200 μm and a resealable layer having thickness of 0.3—2 mm on said gas-barrier film layer, and said blood-collecting tube containing a blood specimen including a serum layer and a clot layer separated by a serum separating agent layer;

introducing a needle having a distal end into the interior of said blood-collecting tube by moving a holding body which holds said needle in a direction toward said film stopper to cause said distal end of said needle to penetrate said film stopper;

detecting said blood specimen serum separating agent layer by means of a sensor coupled to said holding body and positioned outside of said blood-collecting tube at a predetermined distance forward of said distal end of said needle in the direction of movement of said holding body toward said film stopper;

adjusting the position of said distal end of said needle to be located in said blood specimen serum layer by moving said holding body further in the direction toward said film stopper a distance based on the predetermined distance between said distal end of said needle and said sensor; and drawing only said blood specimen serum layer into said needle from said distal end portion of said needle.

2. The blood specimen sampling method of claim 1, further including a step of piercing said film stopper with an air-introducing needle at least before said blood specimen serum layer is drawn into said needle.

3. The blood specimen sampling method of claim 1, further comprising bonding said resealable layer to said gas-barrier film layer.

4. The blood specimen sampling method of claim 3, wherein said bonding step comprises adhering said resealable layer to said gas barrier film layer with an adhesive.

5. The blood specimen sampling method of claim 1, wherein said film stopper is fused to said opening portion of said blood-collecting tube by fusing said gas-barrier film layer of said film stopper to said opening portion of said blood-collecting tube.

* * * * *